United States Patent [19]

Seta

[11] Patent Number: 4,847,512

[45] Date of Patent: Jul. 11, 1989

[54] METHOD OF MEASURING HUMIDITY BY DETERMINING REFRACTIVE INDEX USING DUAL OPTICAL PATHS

[75] Inventor: Katuo Seta, Tsukuba, Japan

[73] Assignees: Agency of Industrial Science & Technology; Ministry of International Trade & Industry, Tokyo, Japan

[21] Appl. No.: 171,780

[22] Filed: Mar. 22, 1988

[30] Foreign Application Priority Data

May 2, 1987 [JP] Japan .................................. 62-107966

[51] Int. Cl.$^4$ .............................................. G01N 15/06
[52] U.S. Cl. ......................................... 250/575; 73/335
[58] Field of Search .................. 250/575; 73/335, 336, 73/336.5; 356/436, 437

[56] References Cited

U.S. PATENT DOCUMENTS 4,450,356  5/1984  Murray et al. ....................... 356/437
4,687,337  8/1987  Stewart et al. ...................... 356/437

FOREIGN PATENT DOCUMENTS 3243320  5/1984  Fed. Rep. of Germany ........ 73/335

*Primary Examiner*—David C. Nelms
*Assistant Examiner*—Khaled Shami
*Attorney, Agent, or Firm*—Oblon, Spivak, McClelland, Maier & Neustadt

[57] ABSTRACT

Humidity is measured by alternatively producing two laser beams of different wavelengths at each of which the second differential derivative of the light absorption spectrum of water molecules is zero, dividing each laser beam, passing one divided beam along an optical path of known length through air, passing the other divided beam along an optical path of the same length through vacuum, causing the divided beams to interfere so as to obtain an apparent difference in length between the two optical paths, this difference being due to the difference in the indices of refraction between air and vacuum, calculating the index of refraction of the air at each wavelength from this difference, and calculating the density of water molecules in the air, i.e. the humidity of the air, from the so-obtained indices of refraction.

3 Claims, 4 Drawing Sheets

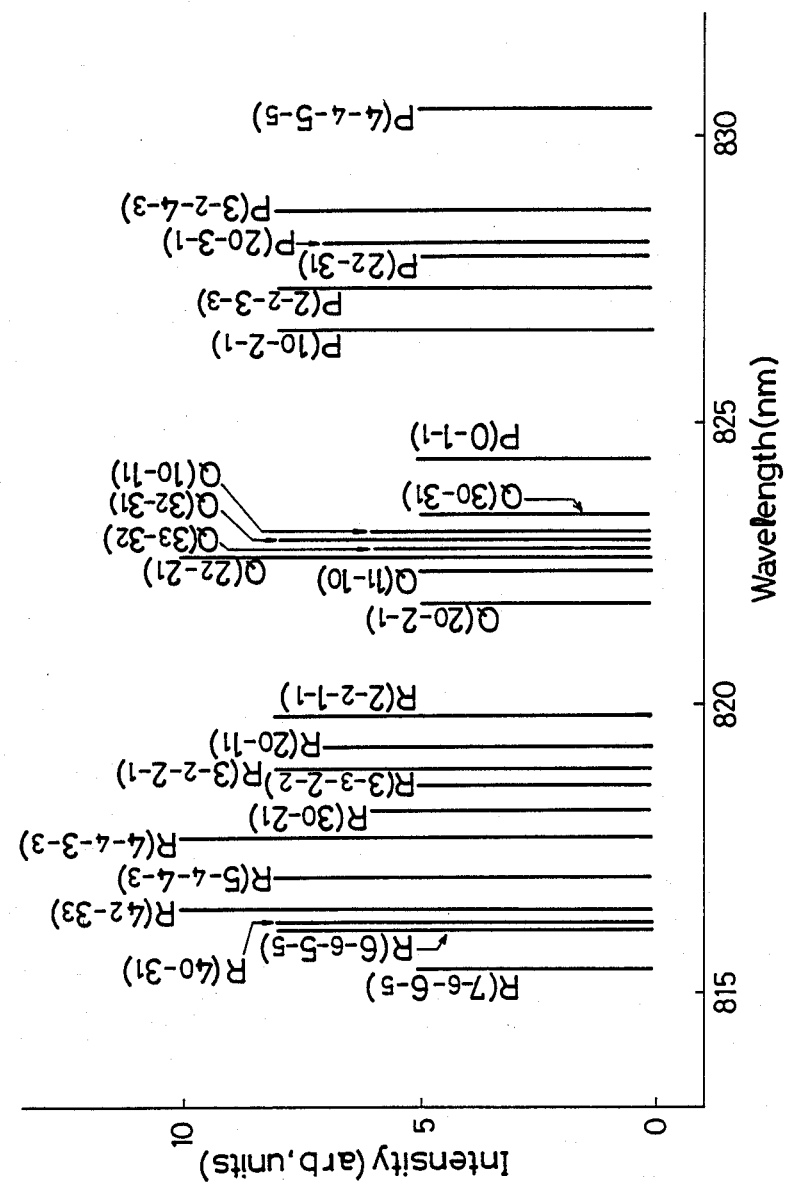

METHOD OF MEASURING HUMIDITY BY DETERMINING REFRACTIVE INDEX USING DUAL OPTICAL PATHS

BACKGROUND OF THE INVENTION

1. Field of the Invention

This invention is related to a method of measuring the density of water molecules in air, namely the humidity of air, and more particularly to a method of measuring humidity with high precision using two laser beams of different wavelengths at each of which the second differential derivative of the absorption spectra of water molecules is equal to zero.

2. Prior Art Statement

The instrument most commonly used for measuring humidity is the dry and wet bulb hygrometer. However, this and other types of hygrometers which rely on a physical phenomenon for measuring humidity are low in precision and difficult to use. What is more, they are unable to measure absolute humidity.

While theoretical studies have been made regarding measurement of humidity by an optical method and it is known that such a method has the potential of providing highly accurate measurement of absolute humidity, there have been very few practical proposal in this connection.

In contrast, in the field of pollution control, two optical methods have been developed and practically applied for the measurement of the concentration harmful gases etc. in the air.

In the first of these methods, the existence and concentration of gases and other substances in the air is determined by observation of the light absorption spectrum (the attenuation component) of the molecules contained in the air. With this method, even the components of mixed gases and trace molecules in the atmosphere can be identified from changes in the absorption spectrum. However, as concentration is determined on the basis of the light intensity of the spectrum, measurement error inevitably arises because of, for example, variation in the intensity of the light source and diffusion of the light. This makes high precision measurement difficult and necessitates various types of processing for compensation.

In the second method, concentration is calculated from the index of refraction of the gas. As this method employs an interferometer, it enables humidity measurement with very high resolution. However, where humidity measurement is to be carried out with respect to a mixed gas such as air, a problem arises as to how to estimate the indices of refraction of molecules other than water molecules and this complicates the post-measurement processing.

OBJECT AND SUMMARY OF THE INVENTION

An object of the invention is to provide a method of measuring humidity which enables simple and high-precision measurement of humidity by measurement of the density of water molecules in air.

According to this invention, this object is realized by a method of measuring humidity comprising the steps of obtaining the second differential derivative of the light absorption spectrum of water molecules, alternately producing two laser beams each of a wavelength at which the value of said second differential derivative becomes zero; alternately dividing said two laser beams into a first divided beam and a second divided beam; transmitting said first divided beam along a first optical path including a section of known length passing through air whose humidity is to be measured; transmitting said second divided beam along a second optical path of the same length as the first optical path and including a section of the same known length through a vacuum; causing the first and second divided beams that have passed along said optical paths to interfere; calculating the apparent difference between the lengths of said first optical path and said second optical path at each said wavelength, said apparent difference arising from the difference between the indices of refraction of air and vacuum; calculating the index of refraction of the air at each said wavelength from the apparent difference; and calculating the water molecule density of the air from the ratio between the indices of refraction at said two wavelengths.

BRIEF DESCRIPTION OF THE DRAWINGS

FIG. 4 is a graph showing the wavelengths absorbed by water vapor.

DETAILED DESCRIPTION OF THE PREFERRED EMBODIMENT

The invention will now be explained in greater detail with respect to the attached drawings.

In the method of measuring humidity according to the present invention, there are produced two laser beams of different wavelengths at each of which the second differential derivative of the light absorption spectrum of water molecules is zero, each laser beam is divided into two beams, one divided beam is passed along an optical path of known length through air, the other divided beam is passed along an optical path of the same length through vacuum, the divided beams are caused to interfere, whereby the apparent difference in length between the two optical paths is obtained, this difference being due to the difference in the indices of refraction between air and vacuum, the index of refraction of the air at each wavelength is calculated from this difference, and the density of water molecules in the air, i.e. the humidity of the air, is calculated from the so-obtained indices of refraction.

The manner of obtaining the first differential derivative of the laser light absorption spectrum will first be explained.

Figure 1:
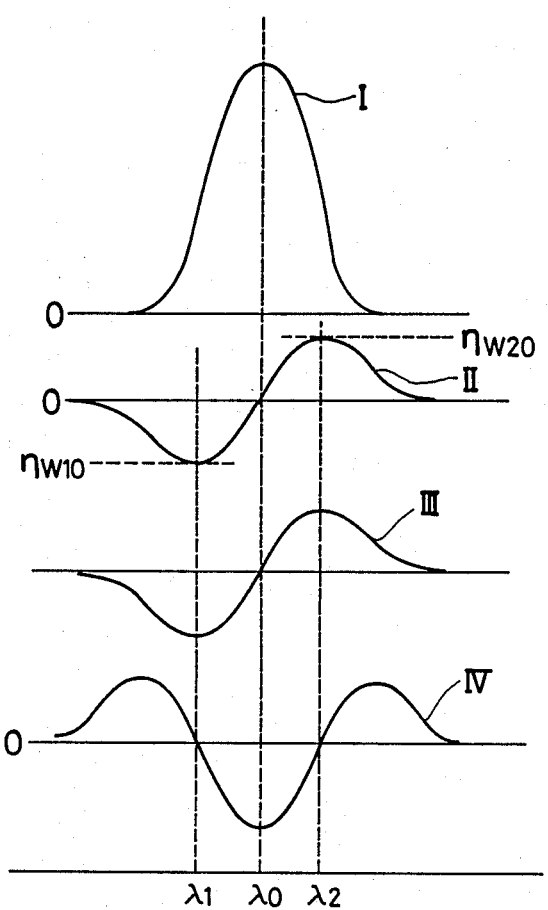
FIG. 1 is a graph showing the distribution relation between light absorption spectrum and index of refraction.

Generally speaking, it is a characteristic of the water molecule light absorption spectrum that the energy absorption is great in regions centered on a plurality of specific frequencies (wavelengths) and that the variation in phase therebetween is large. Therefore, the refractive index varies greatly in the vicinity of the center wavelengths of these regions. The light absorption spectrum centered on the wavelength $\lambda_o$ at which light absorption by the water molecules in air is most pronounced is indicated by curve I in FIG. 1. Curve II in FIG. 1 indicates the change in index of refraction with frequency in the same region, i.e. the distribution characteristics. Curve III in FIG. 1 is the first differential derivative of the light absorption intensity as a function of light frequency, i.e. the reciprocal of wavelength. As will be understood from curves II and II, the curve for the change in index of refraction with wavelength is almost identical in shape with the first differential derivative of the light absorption intensity. Curve IV in FIG. 1 indicates the second differential derivative of the light absorption intensity. Defining the wavelengths $\lambda_1$ and $\lambda_2$ as those at which the second differential curve IV assumes the value of zero, it is found that the indices of refraction at these wavelengths are respectively the minimum value $\eta_{w10}$ and the maximum value $\eta_{w20}$. As shown in FIG. 4, the water vapor molecule has many absorption lines in the region of 810–830 nm, while no atmospheric component other than water vapor has an absorption line in the same region. Thus the index of refraction of dry air exhibits a flat curve with respect to frequency (wavelength).

Two laser beams are produced and stabilized, one at each of the two frequencies $\lambda_1$ and $\lambda_2$ determined in the foregoing manner. As the device for producing the laser beams it is possible to use a semiconductor laser, which is advantageous from the points of ease of handling, controllability, frequency stability etc. (As will be explained later, a single laser is sufficient for alternately producing the two required laser beams.) Semiconductor lasers capable of producing beams with wavelengths absorbed by water molecules are readily available.

Figure 2:
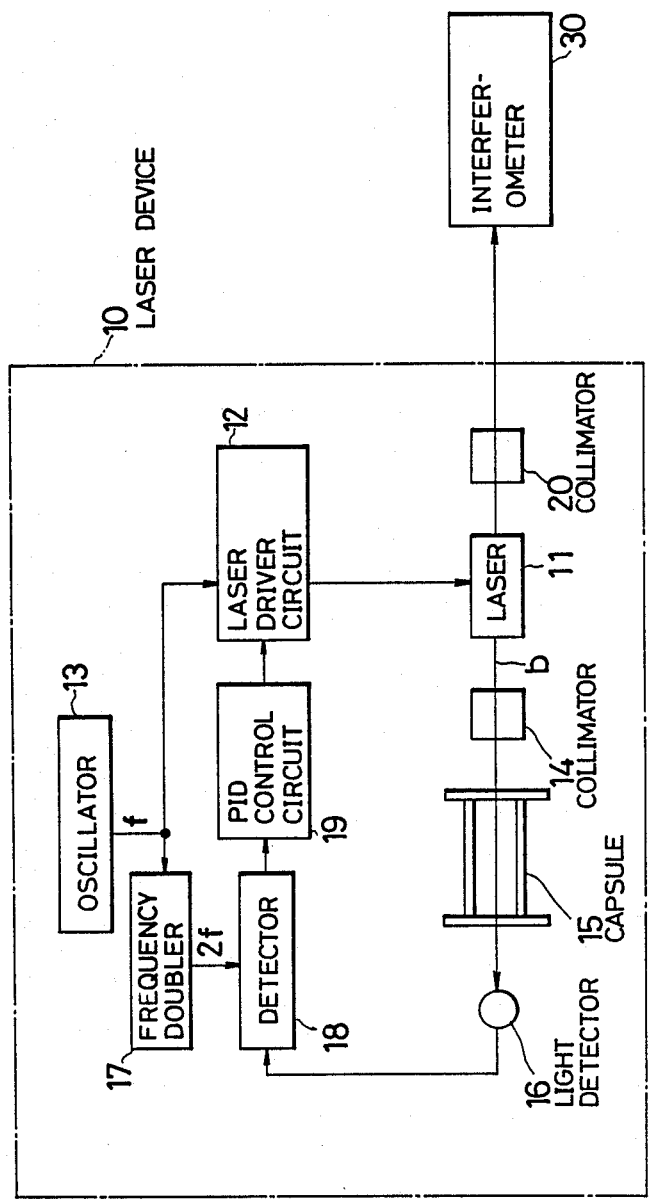
FIG. 2 is a schematic diagram of an embodiment of a laser generation system adapted for use in the present invention.

As one method of causing the semiconductor laser to produce two laser beams with different desired wavelengths there can be used the second differential derivative stabilized laser system 10 shown in FIG. 2.

In this system, the laser beam generating section consists of a semiconductor laser 11, a laser driver circuit 12 and a reference frequency oscillator 13 for producing a signal of frequency f for modulating the output from the circuit 12. The wavelength of the laser beam b produced by the semiconductor laser 11 is modulated as a result of the modulation of the output current of the laser driver circuit 12 by the signal of frequency f from the reference frequency oscillator 13. The wavelength-modulated beam b is transmitted through a collimator 14 to obtain a substantially parallel beam and then through a glass capsule 15 having water vapor sealed therein. It is thereafter converted into an electric signal by a light detector 16. At this time, since at wavelengths in the vicinity of the absorption lines the amount of light absorption by water molecules is dependent on wavelength, the intensity of the detected light will be modulated by the frequency f. Next, using a frequency 2f produced by a frequency doubler 17 as a reference signal, the signal from the light detector 16 is detected by a synchronous detector 18 to obtain the second differential derivative of the absorption spectrum as indicated by curve IV in FIG. 1. This is processed by a PID control circuit 19 which controls a d.c. voltage supplied to the semiconductor laser 11 so as to make the value of the second differential derivative signal zero.

As can be seen from curve IV in FIG. 1, there are two points (at wavelengths $\lambda_1$ and $\lambda_2$) where the second differential derivative becomes zero. It is possible, however, by reversing the polarity of the control signal sent to the semiconductor laser to stabilize the laser output alternately at two different wavelengths. This means that one laser will suffice. The output signal from the PID control circuit 19 is superimposed on the reference signal of frequency f in the semiconductor laser driver circuit 12 and, after appropriate current amplification, is supplied to the semiconductor laser 11. As a result, a laser beam b stabilized at one or the other of the wavelengths at which the second differential derivative curve is at zero is produced by the semiconductor laser 11, collimated by a collimator 20 and forwarded to an interferometer 30 for measurement of refractive index.

Figure 3:
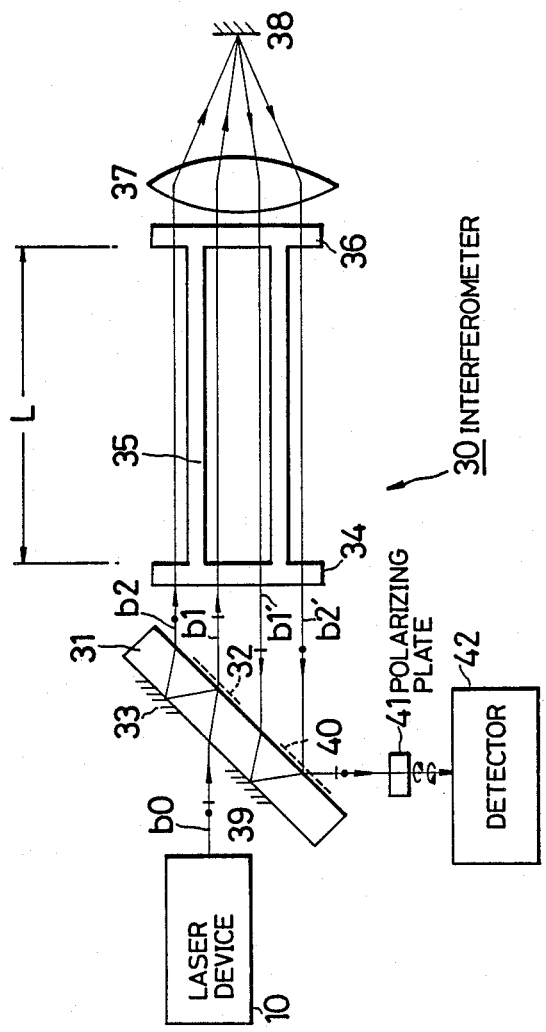
FIG. 3 is an embodiment of an interferometer for measurement of index of refraction adapted for use in the present invention.

Next, the index of refraction of the gas (air) is measured by providing within the laser beam path a section of a known geometric distance and measuring the index of refraction by the interferometer 30. It is not an easy matter to accurately measure the geometric distance used as a reference for the interferometer. Here, therefore, there is used an interferometer which has a vacuum cell 35 and which measures the difference between the index of refraction of the gas and that of the vacuum in the vacuum cell. An example of such an interferometer 30 is shown in FIG. 3. As the light source there is used the second differential derivative stabilized laser system 10 shown in FIG. 2 which is capable of stabilizing at two different wavelengths on the second differential derivative curve of the water molecule absorption spectrum. The laser beam $b_o$ from the laser system 10 is directed toward a plane-parallel plate 31 coated with a transparent polarizing film 32. Of the two beams into which the laser beam $b_o$ is divided by the plane-parallel plate 31, the p polarized beam $b_1$ advances in parallel with beam $b_o$ and the reflected s polarized beam $b_2$ is reflected again by a total reflection film 33 coating the back surface of the plane-parallel plate 31 and thereafter advances in the same direction as the beam $b_o$. The beams b1 and b2 pass through a plate 34 which serves as a window of the vacuum cell 35. The beam $b_1$ passes through the vacuumized interior of the vacuum cell 35, while the beam $b_2$ passes through the surrounding air. Then, after passing through a plane-parallel plate 36, the beams $b_1$ and $b_2$ are reflected by a cat's eye reflector constituted by a lens 37 and a reflecting mirror 38. One beam $b_1'$ of the two reflected beams returns to the plane-parallel plate 31 through the interior of the vacuum cell 35, while the other beam $b_2$ returns through the surrounding air. The beam $b_1'$ is reflected by a total reflection film 39 and the two beams $b_1'$, $b_2'$ are merged along the same path by a polarizing semi-transparent film 40. When the merged beam is passed through a ¼ wavelength polarizing plate 41, there is obtained a linearly polarized beam whose direction of polarization corresponds to the phase difference $\epsilon$ between the two beams. By measuring this direction of polarization using a polarization angle detector 42, it is possible to obtain the phase difference $\epsilon$. The phase difference $\epsilon$ is determined by the difference $\Delta L$. However, since the two beams actually pass along light paths of substantially the same length, it can be presumed that the phase difference is rather due to an apparent difference in length that results from the fact that over the distance L between the plane-parallel plates 34 and 36 one of the beams passes through a vacuum and the other through air.

As the index of refraction in a vacuum is 1, it holds that $$\Delta L = 2(\eta - 1)L = (N + \epsilon)l \tag{1}$$

The index of refraction $\eta$ can be obtained from this equation (1). In this equation, while N stands for an undetermined constant, it can easily be found by once allowing external air into the vacuum cell and recording the phase change as the vacuum state is being restored. After the indices of refraction have been obtained for the two wavelengths, the humidity of the air can be accurately calculated from the equations explained below.

As was stated in the foregoing, two laser beams are adjusted to different wavelengths at each of which the second differential derivative at the absorption spectrum of water molecules in air becomes zero. Let the measured values of the indices of refraction of air at these wavelengths be $\lambda_1$ and $\lambda_2$. Then the index of refraction of a given sample of air can be represented as the sum of the index of refraction of dry air $\eta_d$ and the index of refraction $\eta_w$ resulting from water molecules, as follows $$\eta_1 - 1 = (\eta_{d1} - 1) + (\eta_{w1} - 1) \quad (2)$$
$$= (d/d_0)(\eta_{d10} - 1) + (w/w_0)(\eta_{w10} - 1)$$

$$\eta_2 - 1 = (\eta_{d2} - 1) + (\eta_{w2} - 1) \quad (3)$$
$$= (d/d_0)(\eta_{d20} - 1) + (w/w_0)(\eta_{w20} - 1)$$

In the above equations, d and w are the water molecule concentration (density) of dry air and air whose humidity is being measured, respectively. The subscripts 1 and 2 indicate the values at the first and second wavelengths, while subscript 0 indicates the reference value. In this case, the index of refraction components $\eta_{w1}$ and $\eta_{w2}$ of the water molecules in the air are those for the maximum and minimum values, respectively, so that the difference therebetween is great. On the other hand, in the case of dry air, the wavelengths at which $\eta_{w1}$ and $\eta_{w2}$ occur are very close together and the difference between these two indices of refraction is small. From the above equations (2) and (3) the water molecule density w can be calculated as $$w = \frac{(\eta_1 - 1)(\eta_{d20} - 1) - (\eta_2 - 1)(\eta_{d10} - 1)}{(\eta_{w10} - 1)(\eta_{d20} - 1) - (\eta_{w20} - 1)(\eta_{d10} - 1)} \times w_0 \quad (4)$$

Here, since the difference between $\eta_{d10}$ and $\eta_{d20}$ ($\eta_{d10} - \eta_{d20}$) is very small in comparison with the difference $\eta_{w10} - \eta_{w20}$, the following approximation can be assumed to hold $$w \approx w_0 + (\eta_1 - \eta_2)/(\eta_{w10} - \eta_{w20}) \quad (5)$$

Equation (4) can be used in cases where particularly high measurement precision is required. Otherwise equation (5) will suffice.

As shown schematically in FIG. 2, the device used for this purpose has the second differential derivative stabilized laser system 10 shown schematically in FIG. 2. This system obtains the second differential derivative curve for the water molecules and alternately produces two laser beams of different wavelength such that at each wavelength the value on the curve is zero. These laser beams are received by the interferometer 30 which, on the basis of the relationships explained above, alternately calculates the indices $\eta_1$ and $\eta_2$ and once this has been done it is possible to calculate the density w of the water molecules using either equation (3) or equation (4). When refractive index is measured using an interferometer, the influence of fluctuation in the intensity of the light source is less than in the case where measurement is based on light absorption line intensity. Moreover, as the interferometer is a highly sensitive instrument, the measurement of humidity can be carried out with high resolution.

Thus this invention enables measurement of the water molecule density of air with exceedingly high precision and resolution, and, as such, provides a humidity measuring method which can be very effectively applied in cases where highly accurate measurement is required or where it is necessary to determine whether trace water molecules are present in air. Further, in accordance with this method, once the indices of refraction have been measured at the two frequencies for a reference humidity, it becomes possible to conduct highly accurate absolute measurement. As a result, the apparatus employing this method can be used as a standard against which other hygrometers can be calibrated. Also, the hygrometer employing the method of this invention can be manufactured inexpensively without sacrifice of its intrinsically high performance since apparatuses capable of producing laser beams of identical wavelengths can be readily mass produced.

What is claimed is:

1. A method of measuring humidity comprising the steps of:
   obtaining the second differential derivative of the light absorption spectrum of water molecules;
   alternately producing two laser beams each of a wavelength at which the value of said second differential becomes zero;
   alternately dividing said two laser beams into a first divided beam and a second divided beam;
   transmitting said first divided beam along a first optical path including a section of known length passing through air whose humidity is to be measured;
   transmitting said second divided beam along a second optical path of the same length as the first optical path and including a section of the same known length through a vacuum;
   causing the first and second divided beams that have passed along said optical paths to interfere;
   calculating an apparent difference between the lengths of said first optical path and said second optical path at each said wavelength, said apparent difference arising from the difference between the indices of refraction of air and vacuum;
   calculating the index of refraction of the air at each said wavelength from the apparent difference; and
   calculating the water molecule density of the air from the ratio between the indices of refraction at said two wavelengths.

2. A method according to claim 1, wherein said two laser beams are produced by a single semiconductor laser, a laser beam of one wavelength being produced when the semiconductor laser is supplied with a control signal of a first polarity and the other beam being produced when the semiconductor laser is supplied with a control signal of opposite polarity.

3. A method according to claim 2, wherein the indices of refraction when the value of the second differential derivative becomes zero are the maximum and minimum indices of refraction.

* * * * *